US009116132B2

(12) United States Patent
Wolters et al.

(10) Patent No.: US 9,116,132 B2
(45) Date of Patent: *Aug. 25, 2015

(54) SURFACE SCANNING INSPECTION SYSTEM WITH INDEPENDENTLY ADJUSTABLE SCAN PITCH

(71) Applicant: KLA-Tencor Corporation, Milpitas, CA (US)

(72) Inventors: Christian Wolters, San Jose, CA (US); Juergen Reich, Campbell, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/532,989

(22) Filed: Nov. 4, 2014

(65) Prior Publication Data

US 2015/0055128 A1    Feb. 26, 2015

Related U.S. Application Data

(63) Continuation of application No. 13/413,521, filed on Mar. 6, 2012, now Pat. No. 8,885,158.

(60) Provisional application No. 61/451,592, filed on Mar. 10, 2011.

(51) Int. Cl.
*G01N 21/95* (2006.01)
*G01N 21/956* (2006.01)

(52) U.S. Cl.
CPC .......... *G01N 21/9501* (2013.01); *G01N 21/956* (2013.01); *G01N 2201/06113* (2013.01); *G01N 2201/103* (2013.01)

(58) Field of Classification Search
CPC .................................................. G01N 21/9501

USPC .......... 356/237.1–237.5; 250/492.22, 559.27, 250/559.31
See application file for complete search history.

(56) References Cited

U.S. PATENT DOCUMENTS 6,204,918 B1   3/2001  Isozaki et al.
6,529,270 B1   3/2003  Bills (Continued)

FOREIGN PATENT DOCUMENTS

JP    2000-260376 A    9/2000

OTHER PUBLICATIONS

International Search Report and Written Opinion mailed on Oct. 4, 2012, for PCT Application No. PCT/US2012/028092 filed on Mar. 7, 2012, by KLA-Tencor Corporation, 8 pages.

*Primary Examiner* — Sang Nguyen
(74) *Attorney, Agent, or Firm* — Spano Law Group; Joseph S. Spano (57) ABSTRACT

A surface scanning wafer inspection system with independently adjustable scan pitch and associated methods of operation are presented. The scan pitch may be adjusted independently from an illumination area on the surface of a wafer. In some embodiments, scan pitch is adjusted while the illumination area remains constant. For example, defect sensitivity is adjusted by adjusting the rate of translation of a wafer relative to the rate of rotation of the wafer without additional optical adjustments. In some examples, the scan pitch is adjusted to achieve a desired defect sensitivity over an entire wafer. In other examples, the scan pitch is adjusted during wafer inspection to optimize defect sensitivity and throughput. In other examples, the scan pitch is adjusted to maximize defect sensitivity within the damage limit of a wafer under inspection.

19 Claims, 7 Drawing Sheets

(56) References Cited

U.S. PATENT DOCUMENTS

| | | |
|---|---|---|
| 6,608,676 B1 | 8/2003 | Zhao et al. |
| 8,755,044 B2 * | 6/2014 | Reich et al. .............. 356/237.4 |
| 2003/0103203 A1 | 6/2003 | Isozaki et al. |
| 2004/0076322 A1 | 4/2004 | Guetta |
| 2004/0252295 A1 * | 12/2004 | Miyakawa et al. ........ 356/237.2 |
| 2004/0263835 A1 | 12/2004 | Miyakawa et al. |
| 2006/0103856 A1 | 5/2006 | Miyakawa et al. |
| 2006/0256325 A1 | 11/2006 | Mcmillan et al. |
| 2009/0200279 A1 * | 8/2009 | Li ........................... 219/121.66 |
| 2009/0224180 A1 | 9/2009 | Aigner |
| 2009/0225399 A1 | 9/2009 | Zhao et al. |
| 2010/0093112 A1 | 4/2010 | Takagi et al. |
| 2012/0229802 A1 * | 9/2012 | Wolters et al. ............. 356/237.5 |

* cited by examiner

| MAXIMUM PITCH INCREASE | HIGH SENSITIVITY MODE [WAFERS/HOUR] | HIGH SPEED MODE [WAFERS/HOUR] |
|---|---|---|
| 0% | 36.4 | 61.0 |
| 5% | 36.7 | 61.4 |
| 10% | 36.9 | 61.7 |
| 15% | 37.1 | 62.1 |
| 20% | 37.3 | 62.4 |

SURFACE SCANNING INSPECTION SYSTEM WITH INDEPENDENTLY ADJUSTABLE SCAN PITCH

CROSS REFERENCE TO RELATED APPLICATION

The present application for patent is a continuation of, and claims priority under 35 U.S.C. §120 from U.S. patent application Ser. No. 13/413,521, entitled "Surface Scanning Inspection System With Adjustable Scan Pitch," filed Mar. 6, 2012, which, in turn, claims priority under 35 U.S.C. §119 from U.S. provisional patent application Ser. No. 61/451,592, entitled "Method of Using Pitch Adjustment in SSIS for Sensitivity and T-put Optimization," filed Mar. 10, 2011, the subject matter of each are incorporated herein by reference in their entireties.

TECHNICAL FIELD

The described embodiments relate to systems for wafer inspection, and more particularly to scanning modalities in wafer inspection.

BACKGROUND INFORMATION

Semiconductor devices such as logic and memory devices are typically fabricated by a sequence of processing steps applied to a substrate or wafer. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Inspection processes are used at various steps during a semiconductor manufacturing process to detect defects on wafers to promote higher yield. As design rules and process windows continue to shrink in size, inspection systems are required to capture a wider range of physical defects on wafer surfaces while maintaining high throughput.

One such inspection system is a spinning wafer inspection system that translates and rotates a wafer in a fixed ratio during inspection. The fixed ratio is selected to provide the desired defect sensitivity over the entire wafer under inspection. Improvements to spinning wafer inspection systems are desired to both maintain desired defect sensitivity and improve throughput.

SUMMARY

A scanning wafer inspection system with independently adjustable scan pitch and associated methods of operation are presented. The scan pitch may be adjusted independently from an illumination area on the surface of a wafer. In some examples, scan pitch is adjusted while the illumination area remains constant. In some embodiments, defect sensitivity is adjusted by adjusting the rate of translation of a wafer relative to the rate of rotation of the wafer without additional optical adjustments.

In some examples, the scan pitch is adjusted to achieve a desired defect sensitivity over an entire wafer. By adjusting the scan pitch, defect sensitivity may be controlled by parameter adjustments within a motion controller rather than complex optical actuation.

In another example, the scan pitch is adjusted during wafer inspection to optimize defect sensitivity and throughput. By adjusting the scan pitch during a wafer scan, the defect sensitivity may be matched to the noise signature of the wafer surface over all locations on the wafer resulting in increased throughput.

In yet another example, the scan pitch is adjusted to maximize defect sensitivity within the damage limit of a wafer under inspection. By adjusting scan pitch defect sensitivity may be increased while utilizing a relatively large beam size. The large beam size lowers the power density on the wafer surface resulting in a reduced risk of thermal or photo-chemical damage.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein, as defined solely by the claims, will become apparent in the non-limiting detailed description set forth herein.

BRIEF DESCRIPTION OF THE DRAWINGS

FIG. 2 is a simplified diagram illustrative of a wafer 102 under inspection and an illumination area 102a.

DETAILED DESCRIPTION

Reference will now be made in detail to background examples and some embodiments of the invention, examples of which are illustrated in the accompanying drawings.

Figure 1:
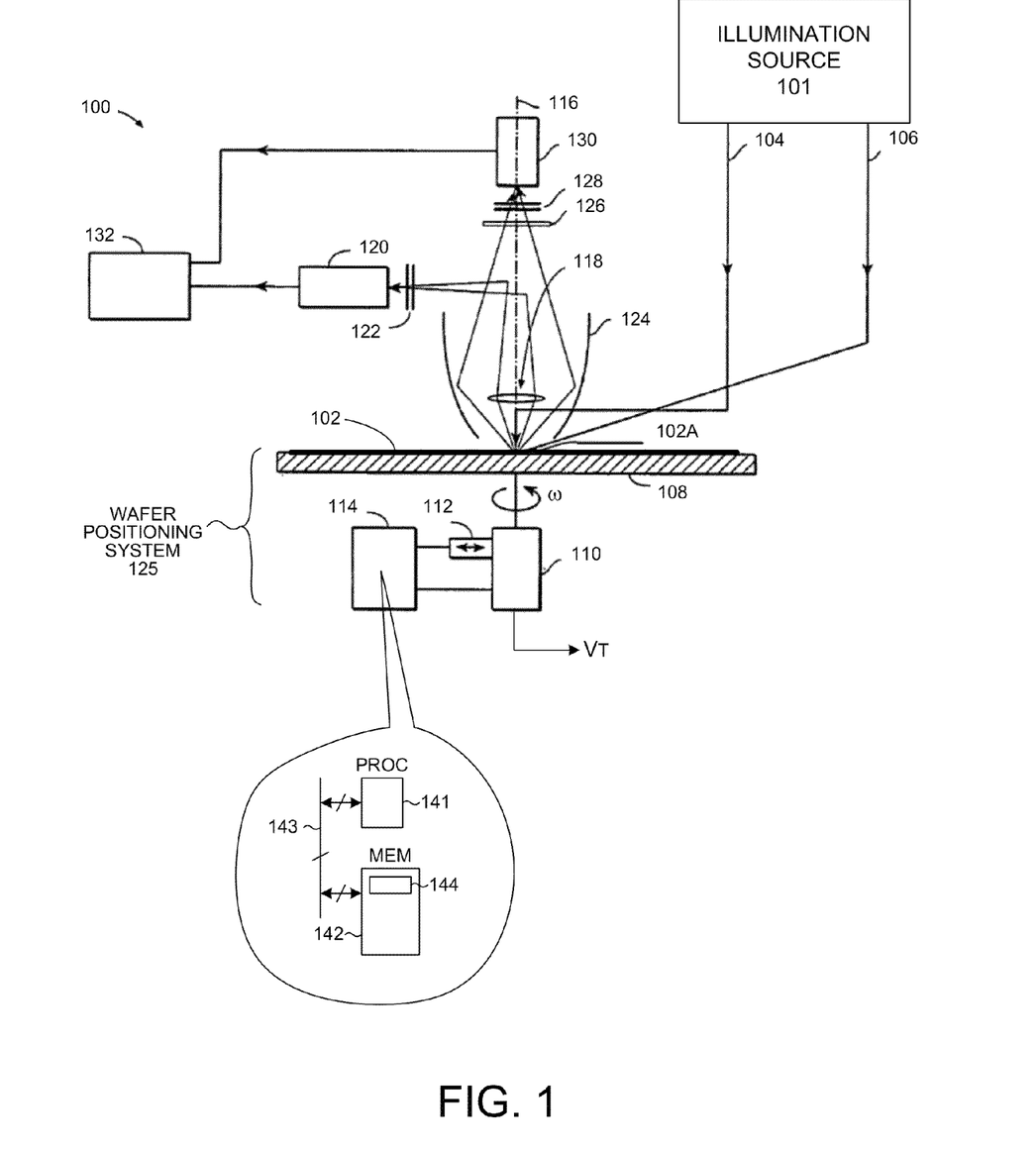
FIG. 1 is a plot illustrative of a spinning wafer inspection system 100.

FIG. 1 is a simplified schematic view of a typical wafer inspection system 100. For simplification, some optical components of the system have been omitted, such as components directing the illumination beams to the wafer. A wafer 102 is illuminated by any of a normal incidence beam 104 and an oblique incidence beam 106 generated by one or more illumination sources 101. The area or spot 102a illuminated by either one or both beams 104, 106 on wafer 102 scatters radiation from the beam(s). The radiation scattered by area 102a along directions close to a line 116 perpendicular to the surface of the wafer and passing through the area 102a is collected and focused by lens collector 118 and directed to a photo-multiplier tube (PMT) 120. Since lens 118 collects the scattered radiation along directions close to the normal direction, such collection channel is referred to herein as the narrow channel and PMT 120 as the dark field narrow PMT. When desired, one or more polarizers 122 may be placed in the path of the collected radiation in the narrow channel.

Radiation scattered by spot 102a of wafer 102, illuminated by either one or both beams 104, 106, along directions away from the normal direction 116 is collected by an ellipsoidal collector 124 and focused through an aperture 126 and optional polarizers 128 to dark field PMT 130. Since the ellipsoidal collector 124 collects scattered radiation along directions at wider angles from the normal direction 116 than lens 118, such collection channel is referred to as the wide channel. The outputs of detectors 120, 130 are supplied to a computer 132 for processing the signals and determining the presence of anomalies and their characteristics.

Various aspects of surface inspection system 100 are described in U.S. Pat. Nos. 6,271,916 and 6,201,601, both of which are incorporated herein by reference. An exemplary surface inspection system is available from KLA-Tencor Corporation of San Jose, Calif., the assignee of the present application.

Figure 2:
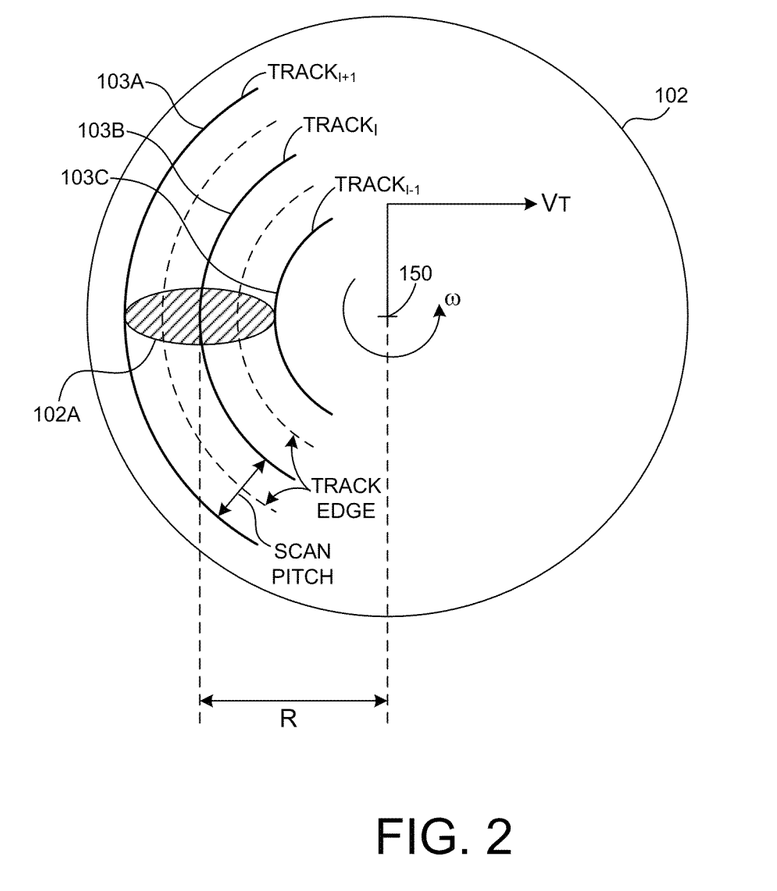

In one embodiment, wafer positioning system 125 includes a wafer chuck 108, motion controller 114, a rotation stage 110 and a translation stage 112. Wafer 102 is supported on wafer chuck 108. As illustrated in FIG. 2, wafer 102 is located with its geometric center 150 approximately aligned the axis of rotation of rotation stage 110. In this manner, rotation stage 110 spins wafer 102 about its geometric center at a specified angular velocity, ω, within an acceptable tolerance. In addition, translation stage 112 translates the wafer 102 in a direction approximately perpendicular to the axis of rotation of rotation stage 110 at a specified velocity, $V_T$. Motion controller 114 coordinates the spinning of wafer 102 by rotation stage 110 and the translation of wafer 102 by translation stage 112 to achieve the desired scanning motion of wafer 102 within wafer inspection system 100.

Any of beams 104 and 106 illuminate an illumination area 102a of wafer 102 that is located a distance, R, from the geometric center of wafer 102. Illumination area 102a is defined (i.e., shaped and sized) by the projection of any of beams 104 and 106 onto the surface of wafer 102. Illumination area 102a may be interchangeably termed the beam spot size or the spot size of wafer inspection system 100.

In an exemplary operational scenario, inspection begins with illumination area 102a located at the geometric center 150 of wafer 102 and then wafer 102 is rotated and translated until illumination area 102a reaches the outer perimeter of wafer 102 (i.e., when R equals the radius of wafer 102). Due to the coordinated motion of rotation stage 110 and translation stage 112, the locus of points illuminated by illumination area 102a traces a spiral path on the surface of wafer 102. The spiral path on the surface of wafer 102 is referred to as an inspection track 103 (not shown). Portions 103a, 103b, and 103c of an exemplary inspection track 103 are illustrated in FIG. 2 as $TRACK_{i+1}$, $TRACK_i$, and $TRACK_{i-1}$, respectively. The distance between adjacent portions of an inspection track (e.g., distance between $TRACK_{i+1}$ and $TRACK_i$) is referred to as the scan pitch of the wafer inspection system 100.

Typically, wafer inspection systems employ a fixed relationship between scan pitch and illumination area during operation. Thus, in typical wafer inspection systems, scan pitch is not adjusted independently from illumination area. Rather, in typical wafer inspection systems, when scan pitch is adjusted, illumination area is scaled according to a fixed relationship. For example, typical wafer inspection systems may offer several operational modes (e.g., fast, low resolution scan and slow, high resolution scan). Each mode may utilize a different scan pitch, but the illumination area (i.e., spot size) corresponding with each mode is also adjusted such that a fixed relationship between spot size and scan pitch is maintained for each mode. The Surfscan® SP1 wafer inspection system manufactured by KLA-Tencor Corporation, San Jose, Calif., is an example of a wafer inspection system that does not adjust scan pitch independently from illumination area.

In one aspect, the scan pitch of wafer inspection system 100 is adjusted independently from illumination area. In one example, the scan pitch is adjusted to achieve a desired defect sensitivity over an entire wafer 102. In another example, the scan pitch is adjusted during inspection of wafer 102. In one operational example, the scan pitch of a wafer under inspection is continuously adjusted as a function of the distance between the illumination area 102a and the geometric center 150 of wafer 102. In yet another example, the scan pitch is adjusted to maximize defect sensitivity within the damage limit of wafer 102.

Referring to FIG. 1, wafer inspection system 100 includes a processor 141 and an amount of computer readable memory 142. As depicted in FIG. 1, by way of example, motion controller 114 includes processor 141 and memory 142, however, processor 141 and memory 142 may be included in other components of wafer inspection system 100. Processor 141 and memory 142 may communicate over bus 143. Memory 142 includes an amount of memory 144 that stores a program code that, when executed by processor 141, causes processor 141 to coordinate the motion of rotation stage 110 and translation stage 112 such that the ratio between the rate of translation of translation stage 112 and the rate of rotation of rotation stage 110 (i.e., scan pitch) is adjusted. In one example, the ratio between the rate of translation of translation stage 112 and the rate of rotation of rotation stage 110 is adjusted as a function of the scan radius, R, between illumination area 102a and the geometric center 150 of wafer 102.

In addition, wafer inspection system 100 may include peripheral devices useful to accept inputs from an operator (e.g., keyboard, mouse, touchscreen, etc.) and display outputs to the operator (e.g., display monitor). Input commands from an operator may be used by processor 141 to generate coordinated motion profiles of rotation stage 110 and translation stage 112. The resulting coordinated motion profiles may be graphically presented to an operator on a display monitor.

Achieving a desired defect sensitivity is a primary performance objective of a wafer inspection system. Defect sensitivity may be measured in terms of false count onset of the wafer inspection system. In one example, false count onset occurs when a wafer inspection system reports a defect at a particular location on the wafer where no defect in fact exists (e.g., the defect is a noise artifact).

In general, to avoid false count onset and increase defect sensitivity, a wafer inspection system should operate with a high Signal to Noise Ratio (SNR). For a given laser power P, wafer rotational speed, w, and radial scan distance, r, measured from the scan spot to the geometric center of the wafer, the Signal to Noise Ratio (SNR) over an illumination area 102a can be estimated as illustrated in Equation 1, where $R_T$ is the tangential spot size and $R_R$ is the radial spot size.

$$SNR \propto \sqrt{\frac{LaserPower}{\omega RR_T}} \left(\frac{1}{R_R}\right) \qquad (1)$$

The relationship illustrated in Equation 1 relates the sensitivity of SNR over the illumination area 102a to spot size (i.e., $R_T$ and $R_R$), laser power, and scan speed (i.e., $\omega R$). Exemplary techniques for managing illumination energy based on adjusting spot size, beam intensity, and spin rate are described in U.S. patent application Ser. No. 11/127,280 by applicant KLA-Tencor Corp. published on Nov. 16, 2006 in U.S. Patent Publication No. US2006/0256325 A1, the entirety of which is incorporated herein by reference.

However for situations where the detection sensitivity is limited by wafer surface noise and other detection noise, the inventors have discovered that defect sensitivity is strongly coupled to scan pitch. The inventors have found that under these circumstances false count onset is particularly driven by SNR at the edge of the inspection track. Due to the energy distribution of a Gaussian beam on the wafer, changes in scan pitch have a significant effect on SNR at the track edge. Thus, defect sensitivity and throughput may be further optimized to meet user objectives based on adjustment of scan pitch independently from illumination area during wafer inspection.

The inventors have discovered that false count onset first occurs in portions of wafer 102 located near the track edge. Based on the appearance of these false counts, it appears as if a defect exists halfway between two adjacent scan tracks, when in fact, none exists. False count onset at the track edges (i.e., between adjacent track locations) is enhanced because the portions of wafer 102 located at the track edges is illuminated by the tails of a typical Gaussian radiation source, rather than the peak of the Gaussian radiation source. In this region, defect detection is driven by combining defect signals of two adjacent track locations. This combination compounds the detection noise of the two adjacent track locations. As a result, for a given noise background, it is more likely that two moderate noise events are combined to result in the onset of false counts.

Figure 3:
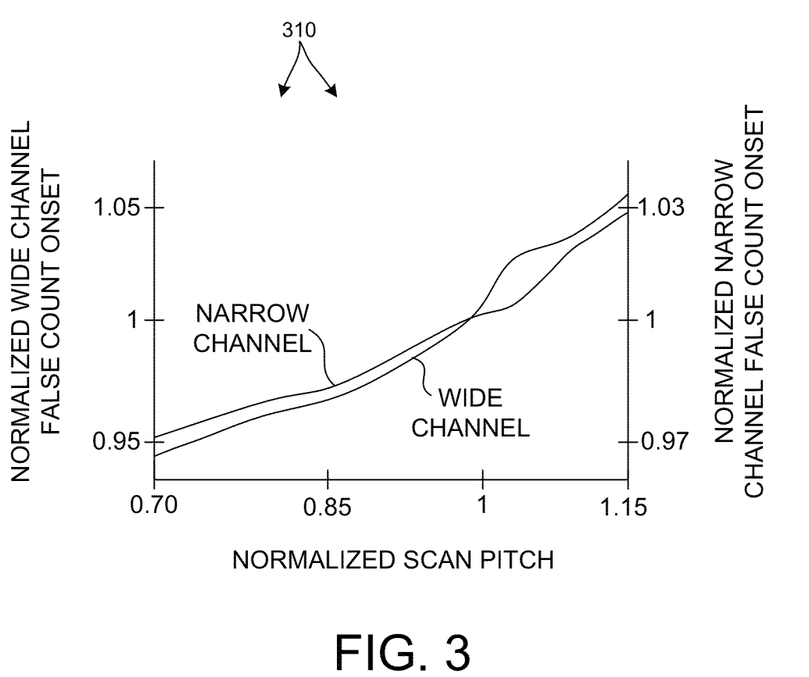
FIG. 3 is a plot 310 illustrative of the defect sensitivity as a function of track pitch for a Surfscan® SP3 wafer inspection system manufactured by KLA-Tencor Corporation, San Jose, Calif.

FIG. 3 is a plot 310 illustrative of the defect sensitivity as a function of track pitch for a Surfscan® SP3 wafer inspection system manufactured by KLA-Tencor Corporation, San Jose, Calif. Plot 310 illustrates that false count onset is coupled to scan pitch at the edge of a track. As illustrated in FIG. 3, the defect size associated with false count onset for both the wide detection channel and the narrow detection channel are plotted as a function of track pitch. In all cases the beam size was held constant. A range of scan pitch values ranging from 70% to 115% of the nominal scan pitch value were tested and the results plotted in FIG. 3. As illustrated, a 10% change in defect sensitivity on the wide channel and a 6% change in defect sensitivity on the narrow channel may result from adjusting the scan pitch within the illustrated range. Although FIG. 3 illustrates the sensitivity of false count onset on scan pitch in one non-limiting example, other operational examples illustrating different sensitivities may be contemplated.

Figure 4:
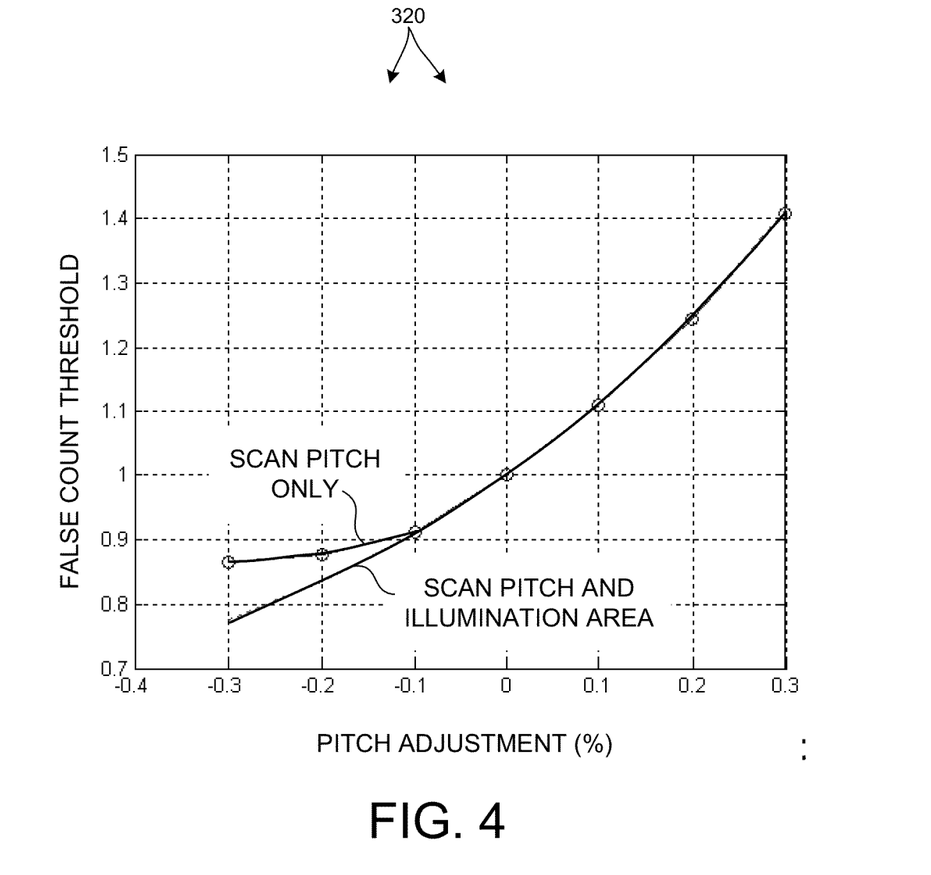
FIG. 4 is a plot 320 illustrative of a simulation of the normalized false count onset threshold as a function of changed in scan pitch.

FIG. 4 is a plot 320 illustrative of a simulation of the normalized false count onset threshold as a function of changes in scan pitch. Two cases are illustrated. In one case, both the scan pitch and beam size are adjusted together in a fixed relationship. In the other case, scan pitch is adjusted independently from illumination area. More specifically, only scan pitch is adjusted and illumination area remains constant. As illustrated in FIG. 4, within a range between −10% and 20% of nominal scan pitch, false count onset performance based on changing scan pitch independently from illumination compared to changing both scan pitch and beam size is practically the same. In other words, the expense and complication of adjusting illumination area can be avoided while controlling defect sensitivity by scan pitch adjustment alone.

Analogously, in certain situations, throughput can be improved by increasing scan pitch without unacceptable losses in defect sensitivity. For inspection scenarios where the achieved inspection defect sensitivity is greater than a desired defect sensitivity, scan pitch can be increased to improve throughput. In some embodiments, the scan pitch may be increased without changing illumination area (as illustrated in FIG. 4) while maintaining a desired defect sensitivity. In this manner, throughput can be enhanced without a penalty on defect sensitivity simply by scanning at a fixed illumination area with a larger scan pitch. Although FIG. 4 illustrates a scan pitch adjustment range between −10% and 20% of nominal scan pitch, other operational ranges may also be contemplated. For example, defect sensitivity may be tuned by adjusting scan pitch independently from illumination area within a range between −25% and 25% of nominal scan pitch. In another example, defect sensitivity may be tuned by adjusting scan pitch independently from illumination area within a range between −50% and 50% of nominal scan pitch. In yet another example, defect sensitivity may be tuned by adjusting scan pitch independently from illumination area within a range between −100% and 100% of nominal scan pitch.

Figure 5:
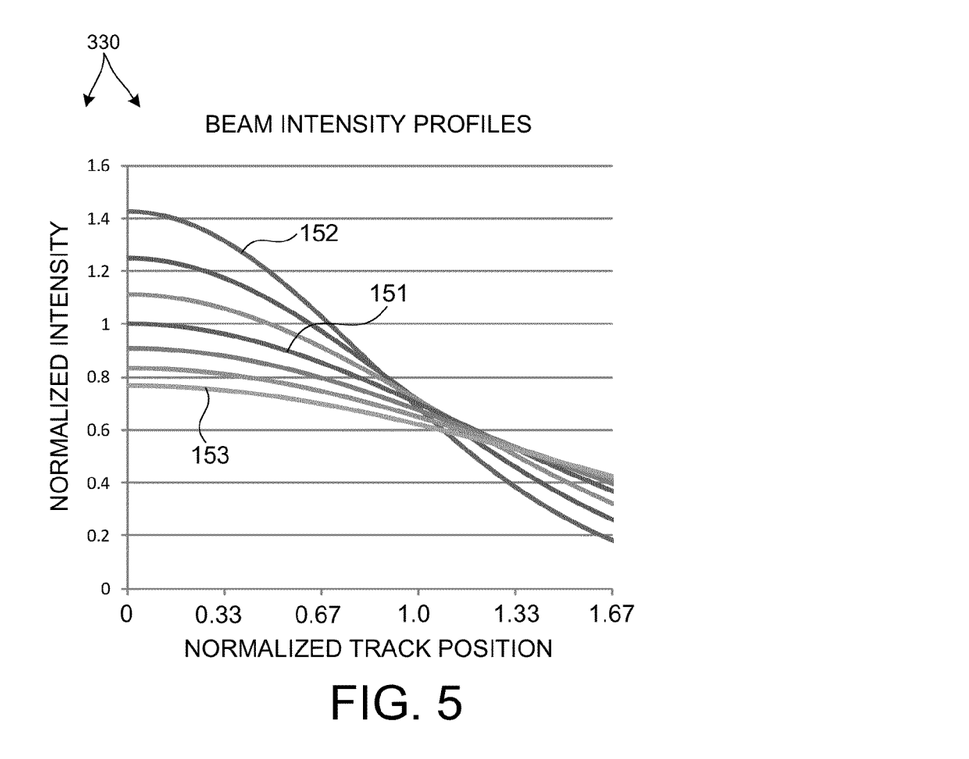
FIG. 5 illustrates a plot 330 that highlights simulation results indicating the beam intensity profiles of different beam sizes at wafer level.
Figure 6:
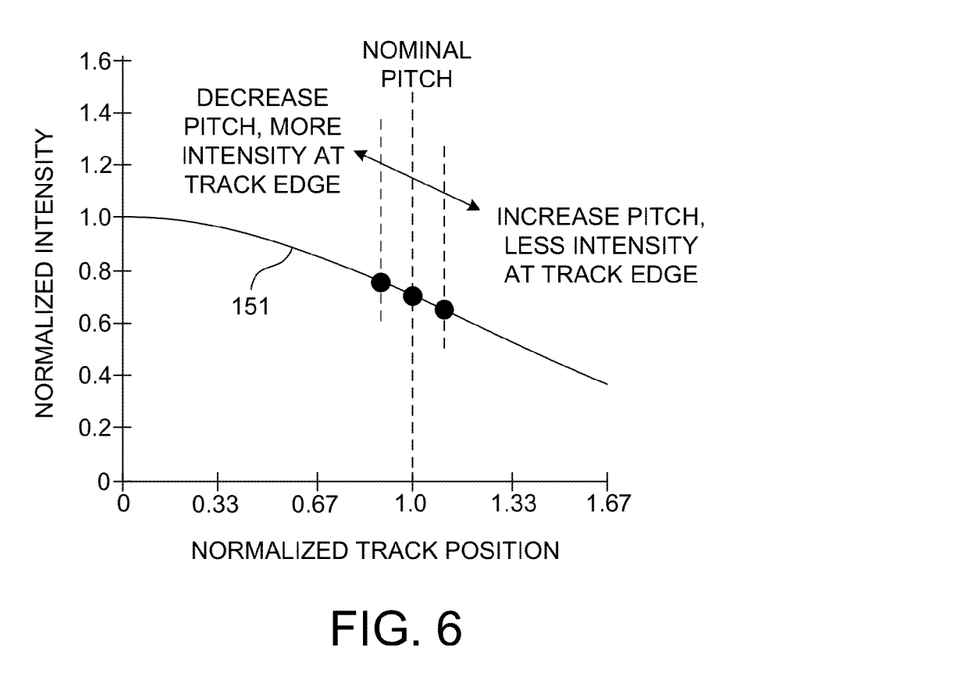
FIG. 6 illustrates a plot that highlights simulation results indicating changes in beam intensity at the track edges based on scan pitch adjustment for a fixed beam size.

FIG. 5 illustrates a plot 330 that highlights simulation results indicating the beam intensity profiles of different beam sizes at wafer level. Each beam has the same total illumination power, only the illumination area is different. For example, beam intensity profile 151 represents a nominal beam size, while beam intensity profiles 152 and 153 represent beam sizes that are 30% smaller and 30% larger than the nominal beam size, respectively. Each beam intensity profile is plotted as a function of distance from the track center. A normalized track position equal to one represents the track edge. As illustrated, significant changes in beam size result in relatively small changes in beam intensity near the track edge (e.g., at normalized track position equal to one). Because, the beam intensity at the tails of a Gaussian shaped beam is relatively independent of beam size, it can be understood that changing beam size without a change in total illumination power has a limited effect on false count onset at track edges. Moreover, precise control of beam size does not yield significant improvements in false count onset at track edges. FIG. 6 illustrates the beam intensity profile 151 illustrated in FIG. 5. As illustrated, small changes (e.g., 10%) in scan pitch result in significant changes in beam intensity near the resulting track edge. Moreover, precise control of scan pitch can yield significant improvements in false count onset at track edges. Thus, a wafer inspection system 100 that adjusts scan pitch independently from illumination area is able to precisely control defect sensitivity vis-a-vis false count onset at track edges.

The cost of wafer inspection system 100 may be reduced because the cost associated with adjusting scan pitch as discussed herein is less than the cost associated with precise optical subsystems necessary for beam shaping. In particular, a wafer inspection system 100 may include a limited number of operational modes (e.g., three modes) and a beam shaping adjustment mechanism that only adjusts the beam shape when changing modes. Otherwise, when operating in a particular mode, all fine tuning of defect sensitivity is achieved by adjustment of scan pitch while beam shape remains constant.

Figure 9:
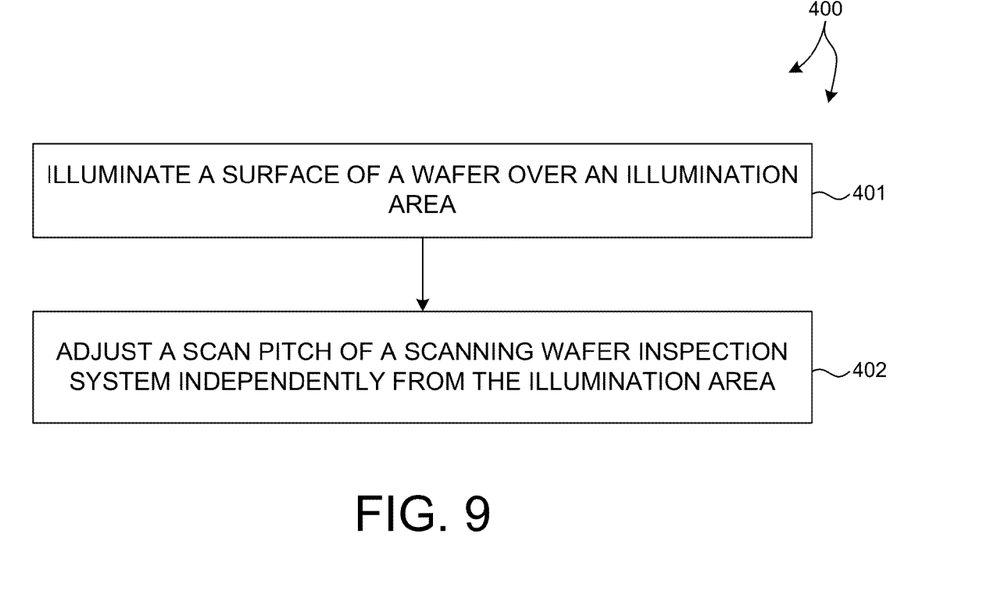
FIG. 9 is a flowchart illustrative of a method 400 of adjusting a scan pitch independently from an illumination area of a scanning wafer inspection system.

FIG. 9 is illustrative of a method 400 of adjusting a scan pitch of a scanning wafer inspection system in accordance with the embodiments presented herein. At block 401, a wafer surface is illuminated over an illumination area. At block 402, the scan pitch of a scanning wafer inspection system is adjusted independently from the illumination area. A number of operational scenarios may be contemplated based on a scanning wafer inspection system with scan pitch adjusted independently from illumination area.

In a first example, the scan pitch may be adjusted independently from the illumination area to meet a particular user requirement (e.g., desired defect sensitivity). In this manner, the defect sensitivity of the wafer inspection system 100 may be adjusted for full wafer scans. This method would be used to adapt the system sensitivity to the user requirements without optical adjustments. The scan pitch can be changed by operation of motion controller 114 as discussed herein. Moreover, in many examples, no optical adjustment (e.g., zooming or power change) is required to achieve the desired defect sensitivity.

Figure 7:
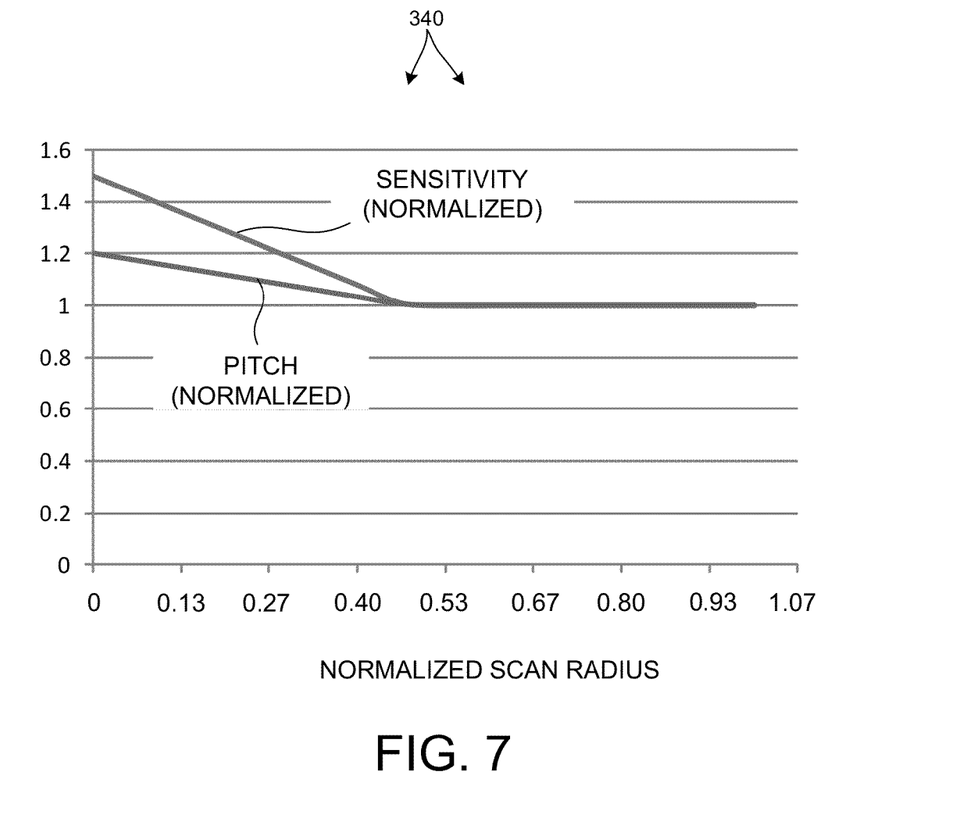
FIG. 7 illustrates a plot 340 that highlights simulation results indicating sensitivity and scan pitch as a function of scan radius.

In a second example, the scan pitch may be adjusted during inspection of a wafer to maintain sensitivity and boost throughput. As illustrated in FIG. 7, the fundamental sensitivity at the center of the wafer is higher than at the edge. This occurs because the tangential scan velocity may be limited by scan radius (i.e. distance between the illumination area 102a and the geometric center 150 of wafer 102) and the achievable angular velocity of rotation stage 110. Within this operating regime, sensitivity is increased due to reduced tangential scan velocity (see Equation 1) and the opportunity to perform increased sample averaging. In a typical example, a limit on tangential scan velocity is reached to maintain adequate sensitivity and this tangential scan velocity is maintained to the perimeter of wafer 102. For example, this limit is typically reached at a scan radius that is approximately one half of the wafer radius.

In another aspect, the scan pitch of wafer inspection system 100 is increased as the tangential scan velocity is decreased toward the center of wafer 102. In the past, the sensitivity advantage near the center of the wafer was not exploited. However, an increase in scan pitch near the center portion of the wafer 102 that scales with the sensitivity profile would tend to maintain a similar sensitivity throughout the wafer. This results in an increase in throughput without loss of production sensitivity. As illustrated in FIG. 7, the scan pitch is steadily increased by 20% from a scan radius where the tangential scan velocity begins to be reduced (e.g., one half of the wafer radius) to the geometric center of wafer 102. Thus, in general, the scan pitch of wafer inspection system 100 is adjusted independently from illumination area based at least in part on a distance between the geometric center of a wafer and the illumination area to increase throughput while maintaining a desired defect sensitivity.

Figure 8:
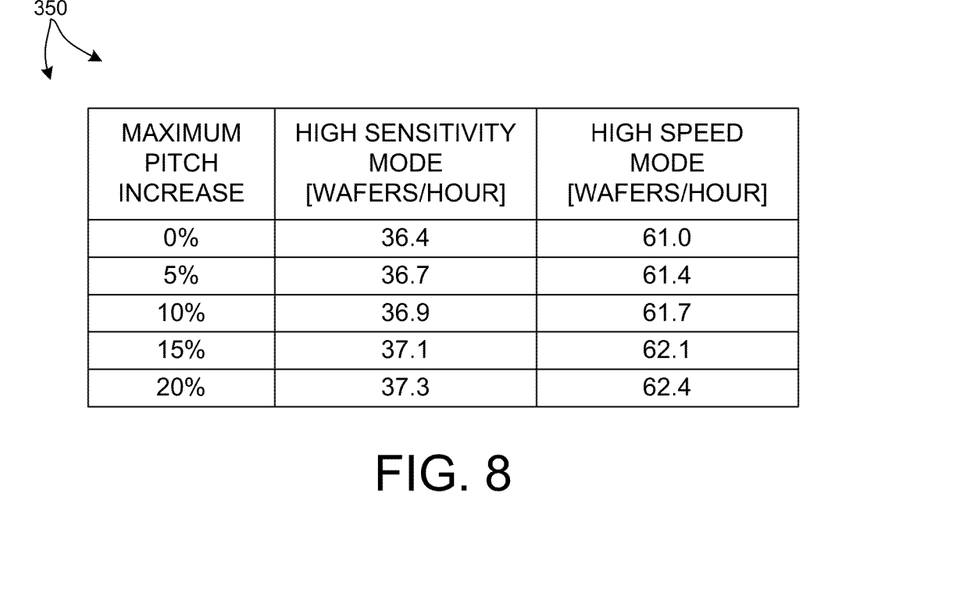
FIG. 8 illustrates a plot 350 of simulation results indicating throughput improvement that may result from increasing scan pitch as a function of wafer radius in the manner illustrated in FIG. 7 for a number of exemplary scenarios.

FIG. 8 illustrates simulation results indicating throughput improvement that may result from increasing scan pitch as a function of wafer radius in the manner illustrated in FIG. 7 for a number of exemplary scenarios. As illustrated, for a scan pitch adjustment of 20%, a 2-3% increase in throughput may be realized. The results illustrated in FIG. 8 are provided as a non-limiting illustrative example. Other operational scenarios may be contemplated that result in different levels of throughput improvement.

Although, in the illustrated example, a limit on tangential scan velocity is reached at a particular scan radius (e.g., half of the wafer radius), this example is not meant to be limiting. Depending on system parameters, a limit on tangential scan velocity may be reached at any scan radius. In some examples, a limit on tangential scan velocity may not be reached at all. In these examples, tangential scan velocity and scan pitch may be continuously scaled as a function of scan radius over the entire wafer.

In a third example, scan pitch may be adjusted to maximize sensitivity within a damage limit of a wafer. As illustrated in Equation 1, as the beam size and tangential scan velocity are decreased, the sensitivity of wafer inspection system 100 increases. However, for a given amount of incident illumination energy, additional gains in sensitivity cannot be made by further decreases in either beam size or tangential scan velocity. One reason is that the wafer surface would be damaged due to incident radiation energy exceeding the damage limit the wafer. For example, depending on materials and inspection conditions, an incident power density between one and ten milliwatts/$\mu m^2$ may bring a wafer surface near the damage limit. However, adjusting the scan pitch to a smaller value improves sensitivity without risk of wafer damage, effectively smearing the incident energy more evenly over the wafer. In this manner, defect sensitivity is further improved by decreasing the scan pitch.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, the the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. In one example, wafer inspection system 100 may include more than one light source (not shown). The light sources may be configured differently or the same. For example, the light sources may be configured to generate light having different characteristics that can be directed to a wafer at the same or different illumination areas at the same or different angles of incidence at the same or different times. The light sources may be configured according to any of the embodiments described herein. In addition one of the light sources may be configured according to any of the embodiments described herein, and another light source may be any other light source known in the art. In another example, wafer inspection system 100 may be a multi-spot system. In some embodiments, a multi-spot system may illuminate the wafer over more than one illumination area simultaneously. The multiple illumination areas may spatially overlap. The multiple illumination areas may be spatially distinct. In some embodiments, a multi-spot system may illuminate the wafer over more than one illumination area at different times. The different illumination areas may temporally overlap (i.e., simultaneously illuminated over some period of time). The different illumination areas may be temporally distinct. In general, the number of illumination areas may be arbitrary, and each illumination area may be of equal or different size, orientation, and angle of incidence. In yet another example, wafer inspection system 100 may be a scanning spot system with one or more illumination areas that scan independently from any motion of wafer 102. In some embodiments an illumination area is made to scan in a repeated pattern along a scan line. The scan line may or may not align with the scan motion of wafer 102. Although as presented herein, wafer positioning system 125 generates motion of wafer 102 by coordinated rotational and translational movements, in yet another example, wafer positioning system 100 may generate motion of wafer 102 by coordinating two translational movements. For example motion wafer positioning system 125 may generate motion along two orthogonal, linear axes (e.g., X-Y motion). In such embodiments, scan pitch may be defined as a distance between adjacent translational scans along either motion axis. In such embodiments, a wafer inspection system includes an illumination source and a wafer positioning system. The illumination source supplies an amount of radiation to a surface of a wafer over an illumination area. The wafer positioning system moves the wafer in a scanning motion characterized by a scan pitch (e.g., scanning back and forth in one direction and stepping by an amount equal to the scan pitch in the orthogonal direction). The wafer positioning system includes a motion controller that adjusts the scan pitch independently from the illumination area. Accordingly, various modifications, adaptations, and combinations of various features of the described embodiments can be practiced without departing from the scope of the invention as set forth in the claims.

What is claimed is:

1. A wafer inspection system comprising:
   an illumination source operable to supply an amount of radiation to a surface of a wafer over an illumination area; and
   a wafer positioning system for moving the wafer in a scanning motion characterized by a scan pitch, the wafer positioning system including,
      a motion controller operable to adjust the scan pitch independently from the illumination area to achieve a desired defect sensitivity over the wafer, wherein the scan pitch is adjusted based at least in part on a distance between the geometric center of the wafer and a location of the illumination area on the surface of the wafer.

2. The wafer inspection system of claim 1, wherein the illumination area remains constant as the scan pitch is independently adjusted.

3. The wafer inspection system of claim 1, wherein the scan pitch is adjusted while scanning the wafer.

4. The wafer inspection system of claim 3, wherein the scan pitch is continuously adjusted from a first scan pitch to a second scan pitch over a portion of the wafer.

5. The wafer inspection system of claim 1, wherein the scanning motion involves simultaneously rotating the wafer about the geometric center of the wafer and translating the geometric center of the wafer, wherein a rate of translation of the wafer relative to a rate of rotation of the wafer determines the scan pitch.

6. The wafer inspection system of claim 1, wherein the scan pitch is adjusted based at least in part on a desired defect sensitivity.

7. The wafer inspection system of claim 6, wherein the scan pitch is adjusted to maintain the desired defect sensitivity over the entire wafer with a maximum inspection speed for the entire wafer.

8. The wafer inspection system of claim 6, wherein the scan pitch is adjusted to a maximum defect sensitivity within a damage limit of the wafer.

9. A method of wafer inspection comprising:
   illuminating a surface of a wafer over an illumination area; and
   adjusting a scan pitch of a scanning wafer inspection system independently from the illumination area, wherein the adjusting of the scan pitch is based at least in part on maintaining a desired defect sensitivity over the entire wafer with a maximum inspection speed for the entire wafer.

10. The method of wafer inspection of claim 9, wherein the adjusting of the scan pitch of the scanning wafer inspection system involves adjusting the scan pitch while scanning the wafer.

11. The method of wafer inspection of claim 9, wherein the scanning wafer inspection system is operable to simultaneously rotate a wafer about a geometric center of the wafer and translate the geometric center of the wafer, and wherein the adjusting of the scan pitch involves changing a rate of translation of the wafer relative to a rate of rotation of the wafer.

12. The method of wafer inspection of claim 11, wherein the adjusting of the scan pitch is based at least in part on a distance between the geometric center of the wafer and a location of the illumination area on the surface of the wafer.

13. The method of wafer inspection of claim 9, wherein the adjusting of the scan pitch is based at least in part on maximizing a defect sensitivity within a damage limit of the wafer.

14. A scanning wafer inspection system comprising:
   an illumination source operable to supply an amount of radiation to a surface of a wafer over an illumination area; and
   a non-transitory, computer-readable medium including,
      code for causing a computer to adjust a scan pitch of the scanning wafer inspection system independently from the illumination area, wherein the scan pitch is adjusted based at least in part on maximizing a defect sensitivity within a damage limit of the wafer.

15. The scanning wafer inspection system of claim 14, wherein the scan pitch of the scanning wafer inspection system is adjusted while scanning the wafer.

16. The scanning wafer inspection system of claim 14, wherein the scanning wafer inspection system is operable to simultaneously rotate the wafer about a geometric center of the wafer and translate the geometric center of the wafer, and wherein the scan pitch is adjusted by changing a rate of translation of the wafer relative to a rate of rotation of the wafer.

17. The scanning wafer inspection system of claim 16, wherein the scan pitch is adjusted based at least in part on a distance between the geometric center of the wafer and a location of the illumination area on the surface of the wafer.

18. The scanning wafer inspection system of claim 14, wherein the scan pitch is adjusted based at least in part on maintaining a desired defect sensitivity.

19. The scanning wafer inspection system of claim 18, wherein the scan pitch is adjusted based at least in part on maintaining the desired defect sensitivity over the entire wafer with a maximum inspection speed for the entire wafer.

* * * * *